United States Patent [19]

Thompson et al.

[11] Patent Number: 5,871,508
[45] Date of Patent: Feb. 16, 1999

[54] APPARATUS FOR CARDIAC PACING IN TRANSPLANT

[75] Inventors: David L. Thompson, Fridley; Dwight H. Warkentin, St. Paul, both of Minn.

[73] Assignee: Medtronic, Inc., Minneapolis, Minn.

[21] Appl. No.: 908,142

[22] Filed: Aug. 6, 1997

[51] Int. Cl.⁶ .................................................. A61N 1/368
[52] U.S. Cl. ................................................................ 607/9
[58] Field of Search ................................. 607/9, 37, 5, 4

[56] References Cited

U.S. PATENT DOCUMENTS

| | | |
|---|---|---|
| D. 358,583 | 5/1995 | Winkler ................................ D14/106 |
| 3,937,226 | 2/1976 | Funke . |
| 4,088,140 | 5/1978 | Rockland et al. . |
| 4,181,133 | 1/1980 | Kolenik et al. . |
| 4,354,497 | 10/1982 | Kahn . |
| 4,365,639 | 12/1982 | Goldreyer . |
| 4,374,382 | 2/1983 | Markowitz . |
| 4,379,459 | 4/1983 | Stein . |
| 4,411,268 | 10/1983 | Cox . |
| 4,412,541 | 11/1983 | Schaldach et al. . |
| 4,485,813 | 12/1984 | Anderson . |
| 4,548,203 | 10/1985 | Tacker, Jr. et al. . |
| 4,556,063 | 12/1985 | Thompson et al. . |
| 4,630,611 | 12/1986 | King . |
| 4,708,145 | 11/1987 | Tacker, Jr. et al. . |
| 4,750,494 | 6/1988 | King . |
| 4,754,753 | 7/1988 | King . |
| 4,905,707 | 3/1990 | Davies et al. . |
| 4,928,688 | 5/1990 | Mower . |
| 4,969,463 | 11/1990 | Dahl et al. . |
| 4,987,897 | 1/1991 | Funke . |
| 5,052,388 | 10/1991 | Sivula et al. . |
| 5,107,834 | 4/1992 | Ideker et al. . |
| 5,127,404 | 7/1992 | Wyborny et al. . |
| 5,139,028 | 8/1992 | Steinhaus et al. . |
| 5,197,480 | 3/1993 | Gebhardt . |
| 5,209,229 | 5/1993 | Gilli . |
| 5,243,978 | 9/1993 | Duffin ........................................ 607/11 |
| 5,243,979 | 9/1993 | Stein ......................................... 607/20 |
| 5,281,219 | 1/1994 | Kallok ....................................... 607/42 |
| 5,282,837 | 2/1994 | Adams et al. .............................. 607/5 |
| 5,330,513 | 7/1994 | Nichols et al. ............................ 607/32 |
| 5,331,966 | 7/1994 | Bennett et al. . |
| 5,345,362 | 9/1994 | Winkler ................................... 361/681 |
| 5,366,486 | 11/1994 | Zipes et al. ................................. 607/5 |
| 5,402,794 | 4/1995 | Wahlstrand et al. . |
| 5,403,356 | 4/1995 | Hill et al. ................................. 607/14 |
| 5,447,519 | 9/1995 | Peterson ..................................... 607/5 |
| 5,476,503 | 12/1995 | Yang ....................................... 607/129 |
| 5,507,784 | 4/1996 | Hill ......................................... 607/14 |
| 5,514,161 | 5/1996 | Limousin .................................... 607/9 |
| 5,540,729 | 7/1996 | Weijand ................................... 607/35 |
| 5,549,654 | 8/1996 | Powell ..................................... 607/32 |
| 5,584,867 | 12/1996 | Limousin .................................... 607/9 |
| 5,601,615 | 2/1997 | Markowitz ................................ 607/28 |

FOREIGN PATENT DOCUMENTS

WO96/25977  8/1996  WIPO ............................ A61N 1/37

OTHER PUBLICATIONS

Bipolar Atrial Triggered Pacing to Restore Normal Chronotropic Responsiveness in an Orthotopic Cardiac Transplant Patient (Pace vol. 14 Oct. By; Salem Kacet et al.

Recipient–Donor Atrial Synchronization Benefits Acute Hemodynamics After Orthotopic Heart Transplantation (How to Pace a Transplanted Heart vol. 7 No. 1 Jan./Feb. 1988) By James B. McClurken et al).

An Example of How to Pace a Patient with a Heart Transplanttion (The Journal of Heart Transplantation vol. 7 No. 1 Jan./Feb. 1988) by Georg Osterholser et al.

Allograft Diastolic Dysfunction and Chronotropic Incompetence Limit Cardiac Output Response to Exercise Tow to Six Years After Heart Transplantation The Journal of Heart & Lung transplantation vol. 14 No. 1 part 1 By kao et al.

*Primary Examiner*—Scott M. Getzow
*Attorney, Agent, or Firm*—Michael B. Atlass; Harold R. Patton

[57] ABSTRACT

Pacemaker designed for support of both orthotopic and heterotopic transplants has three lead bore connector block assembly and dedicated or dedictable amplifiers for pacing and sensing configurations unique to transplant situations. The provision of definable amplifier assignments allows for enhanced sensing, capture detection and therapy.

12 Claims, 5 Drawing Sheets

APPARATUS FOR CARDIAC PACING IN TRANSPLANT

FIELD OF INVENTION

This invention relates to the application of cardiac pacing technologies to heart transplants.

BACKGROUND

Heart transplantation is a therapeutic option in the management of end stage heart failure. Two methods of surgical transplantation are typically done; orthotopic or heterotopic. In the orthotopic technique, the donor heart is attached to a partial remnant of the recipient's native right and left atria, essentially replacing the recipient heart chambers. In the heterotopic technique, the donor heart is implanted along side and is attached to the recipient heart such that it augments the recipient's cardiac output. FIG. 1a shows what the completed surgical heterotopic transplant looks like, and FIG. 1b illustrates the orthotopic surgery.

Known problems with heterotopic transplant include the progressive deterioration observed in the recipient left ventricular function and reduced exercise capacity due to the competitive contraction of the two hearts; with the donor left ventricle generating a much higher afterload for the failing recipient left ventricle.

Additionally (in both described transplant techniques), the donor heart is denervated, therefore its resting rate (typically near 90 bpm) exceeds that of the recipient sinus rate. Further, the donor heart rate response to exercise is attenuated, if present at all. Finally, the recipient atrium often develops arrhythmias.

Similar problems may develop with xenotransplants, such as with the use of baboon hearts or genetically altered porcine hearts transplanted into humans.

Because of these and other potential problems, an implantable electrical stimulus generator could be useful if designed to meet the needs of this situation.

A modified pacemaker that can pace at multiple sites and preferably also sense at multiple sites can be used to alleviate the problems described in transplantation described above.

Cardiac electrical stimulation has a long history with implantable cardiac stimulators going back perhaps 40 years. Only recently however have the implanted devices found use for multiple lead configurations. Examples include patents assigned to ELA Medical (Limousin et al.) U.S. Pat. No. 5,514,161 and 5,584,867, for example, and there are also patents directed to defibrillators, see for example U.S. Pat. No. 5,282,837 issued to Adams et al. which show leads in the coronary sinus that may be useful in left atrial or left ventricular stimulation.

A typical pacemaker system which could form the basis for most of the requirements for multisite pacing is described in U.S. Pat. No. 5,549,654 issued to Powell, although many other suitable pacing or pacing and/defibrillation implantable device pulse generator (IPG) platforms may be used. A number of designs for Cardiac Assistance devices may also be used. Such devices are described in, for example U.S. Pat. No. 4,411,268 to Cox, and are used in stimulating muscle tissue which has been (or will be) surgically wrapped around the heart while also providing the possibility of direct cardiac pacing. It is also known for example, that optimizing the timing of ventricular pulses, in relation to paced or serial atrial events can assist in Hypertropic Obstructive Cardiomyopathy (HOCM) Therapy. This is demonstrated in the pending PCT patent publication No. WO96/25977, published in August 1996, for example. Also, as described in the Limousin and Limousin et al. patents cited above, bi-atrial pacing can be advantageous.

It is currently recognized in theory that differing pathways for depolarization waves can greatly affect cardiac performance (see Fritz Prinzen, Ph.D. et al. American Heart Journal, 1995:130:1045–1053, for example). Accordingly, there is a need to develop a multisite capable fully configurable pacemaker and/or pacemaker/defibrillator. Of course, there have been numerous devices which have been taught or developed in response to this need, including those described in patents on devices to control ventricular activation sequence (Cohen, U.S. Pat. No. 5,267,289 and 5,174,536 and Goldreyer U.S. Pat. No. 4,365,639), devices for dealing with fibrillation and other arrhythmias (Combs U.S. Pat. No. 5,562,708; Hill U.S. Pat. No. 5,507,784 and 5,403,356; Zipes U.S. Pat. No. 5,366,486; Duffin U.S. Pat. No. 5,243,978; 5,209,229; Adams U.S. Pat. No. 5,158,079; Ideker U.S. Pat. No. 5,107,834; Tacker Jr U.S. Pat. No. 4,708,145 and 4,548,203; and Prystowsky U.S. Pat. No. 4,554,922), devices capable of sensing through multiple, sometimes switchable electrodes (King U.S. Pat. No. 4,630,611 and 4,754,753; Funke U.S. Pat. No. 3,937,226; and Rockland U.S. Pat. No. 4,088,140; Kahn U.S. Pat. No. 4,354,497;; Mower(in which multiple sense electrode sites assist in treating hemodynamic dysfunction) U.S. Pat. No. 4,928,688), devices for switching between stimulation electrodes generally, (for example, in upper airway muscle stimulation Kallok U.S. Pat. No. 5,281,219), in devices for switching between different out of the device sensors or electrodes (Schaldach U.S. Pat. No. 4,412,541); King U.S. Pat. No. 4,750,494; Peterson U.S. Pat. No. 5,447,519; and Yang U.S. Pat. No. 5,476,503), in a device for applying differing parts of a pulse segment to different parts of a defibrillation electrode (in Dahl U.S. Pat. No. 4,969,463), and in devices which use the same electrodes for demand pacing and antitachy breakup pulses (Kolenik U.S. Pat. No. 4,181,133). However none of the aforementioned devices can perform the function herein described and in various aspects they are lacking in the flexibility and ease of configuration or simplicity of circuitry as the device described herein.

Several doctors have attempted to solve these problems with conventional pacemakers. In AN EXAMPLE OF HOW TO PACE A PATIENT WITH A HEART TRANSPLANTATION, by Osterholzer et al., Journal of Heart Transplant 1988;7:23–5, the authors describe the use of a Pacesetter AFP/283, Pacesetter Systems Inc., pacemaker with a two lead system configured with a lead in the recipient atrium (orthotopic transplant) used to sense the native sinus rate and after the shortest programmable delay, pace the donor atrium, which was counted on to pace the donor ventricle. (An additional lead was implanted into a donor ventricle so that if "atrial fibrillation with slow ventricular response in the donor heart requires ventricular stimulation, a simple pulse generator exchange will solve the problem.")

Another study published by McClurken, et al., RECIPIENT-DONOR ATRIAL SYNCHRONIZATION BENEFITS ACUTE HEMODYNAMICS AFTER ORTHOTOPIC HEART TRANSPLANTATION in the Journal of Heart Lung Transplant, 1996; 15:368–70 also described the benefits of timing the donor atrium to follow the recipient sinus rate. The McCracken article limits it study to acute pacing benefits with temporary heart wires.

Kacet, et al., in their article BIPOLAR ATRIAL TRIGGERED PACING TO RESTORE NORMAL CHRONOTROPIC RESPONSIVE IN AN ORTHOTOPIC CARDIAC TRANSPLANT PATIENT, describe native sinus rhythm following set up for orthotopic transplants wherein a bipolar lead splitter is used to provide a way to bring one unipolar lead each to the native and donor atria, one to sense in the native atria and the other to pace in the donor heart. It cannot, of course sense in the donor atrium at all nor can it sense in the native atrium while the donor atrium is being paced. Kacet use this fact to enforce the employ of a long refractory period, which happens to miss some native atrial arrhythmia.

All the foregoing suggests the need for an advanced pacemaker designed to assist in maintaining hemodynamic and natural sinus rate pacing for transplant patients. It would be most beneficial if the pacemaker could be used in both ortho- and heterotopic transplants.

Further, since the advent of transplant monitoring by implantable devices as described for example in U.S. Pat. Nos. 5,402,794 issued to Wahlstrand, et al.,5,197,480 (Gepphardt), 5,139,028(Steinhaus et al.),5,330,513(Nichols et al), 5,331,966(Bennett et al.), and 4,905,707(Davies and Lekholm), an additional benefit can be had from specifically designing a pacemaker for transplants. That is, by sending indications of the state of the transplanted heart, the usual monthly biopsies to determine the state of the transplant tissue can be avoided or ameileorated.

All of the references cited above are incorporated herein in their entireties by this reference so as to provide both background and disclosure for the invention described herein, said invention being described below with reference to the following Figures.

BRIEF DESCRIPTION OF THE DRAWINGS

The foregoing and other aspects and features of the present are described with reference to the detailed description of specific embodiments of the invention which follows, in conjunction with the drawings, wherein.

SUMMARY OF THE INVENTION

An implantable pulse generator (IPG) for pacing is described to provide pacing to a heart transplant patient based on a natural sinus rate detectable from native atria which can be used advantageously for pacing a transplanted heart. In the preferred form three bores are provided to the connector block for connection to three leads the distal ends of which have electrodes for electrical contact to and are connected to a native atrium, a donor heart atrium and a donor heart ventricle. Each bore provides for connection of the distal lead electrodes with sense and pace amplifiers for each lead in a manner to be described in detail below. At minimum the invention requires a native atrial sense circuit, and a pacing circuit for the donor ventricle, however preferred forms provide sensing and pacing circuitry for a second atrium and for the ventricle as well as pacing circuits for both atria to which the leads are connected. Such additional sense amps provide additional capability with respect to gathering accurate EGM data, capture detection in paced chambers and additional flexibility.

Rate responsive pacing which adapts the pacing rate to cardiac output requirements (based on sensor derived information about a patient's activity or body) may also be employed advantageously, especially where the native atrium does not provide a useable sinus rate and also under circumstance where it may be desirable to increase heart rate for therapeutic or other reasons.

A xenograph, for example a genetically modified porcine or baboon heart, may be substituted for a human heart and the invention should need no modification from the description below.

Additionally, sensors or accumulated EGM data may be employed to signal attending physicians regarding the health of the transplanted heart.

DETAILED DESCRIPTION OF THE INVENTION

Figure 1A:
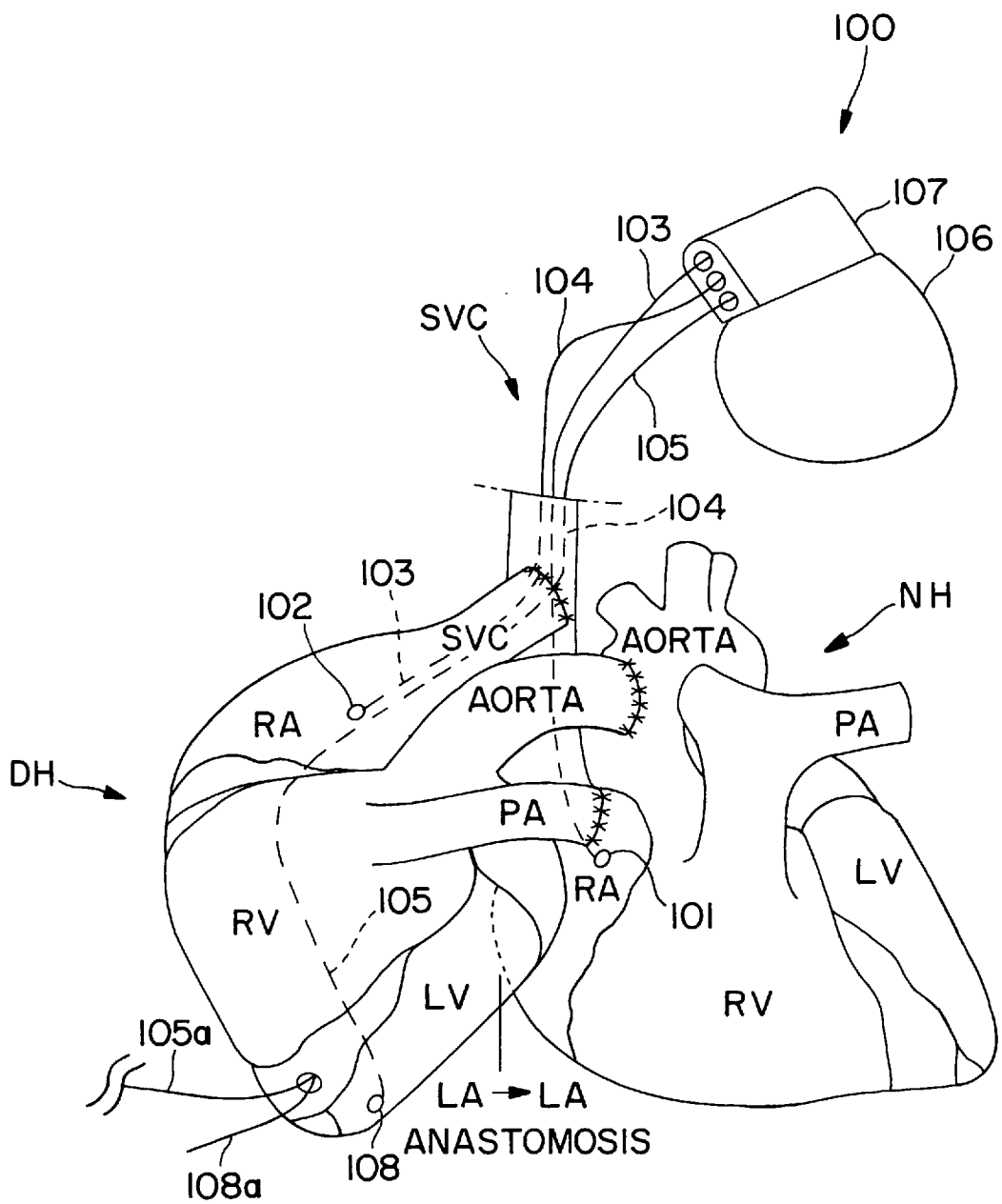
FIGS. 1a and 1b are illustrations of embodiments of this invention employed in heterotopic and orthotopic transplants, respectively.

In FIG. 1a shows an arrangement available for use of the invention in heterotopic transplant is illustrated with the donor heart (DH) sewn in place to the native heart(NH) and the pacemaker 100 connecting its leads transveneously, with the three leads connected to the native right atrium at 101, the DH right atrium at 102 and the donor left ventricle at point 108. through leads 103, 104, and 105, respectively. The most preferred embodiment will have leads 104 and 105 constructed as bipolar leads, but using all three leads in unipolar configuration is acceptable. The leads are connected to a three bore connector block 107 mounted on the pacemaker body or can 106 for electrical connection between the lead conductors and the circuitry for sensing and pacing in the atria and ventricles as described below. Of course, the leads need not be connected to the hearts intravenously through the Superior Vena Cava as shown, for example an epicardial version of lead 105, here (broken) lead end 105a (connected at patch 108a) could instead be connected to the ventricular lead connector bore in connector block 107, and epicardial leads could be used for pacing and sensing in the atria as well.

Figure 1B:
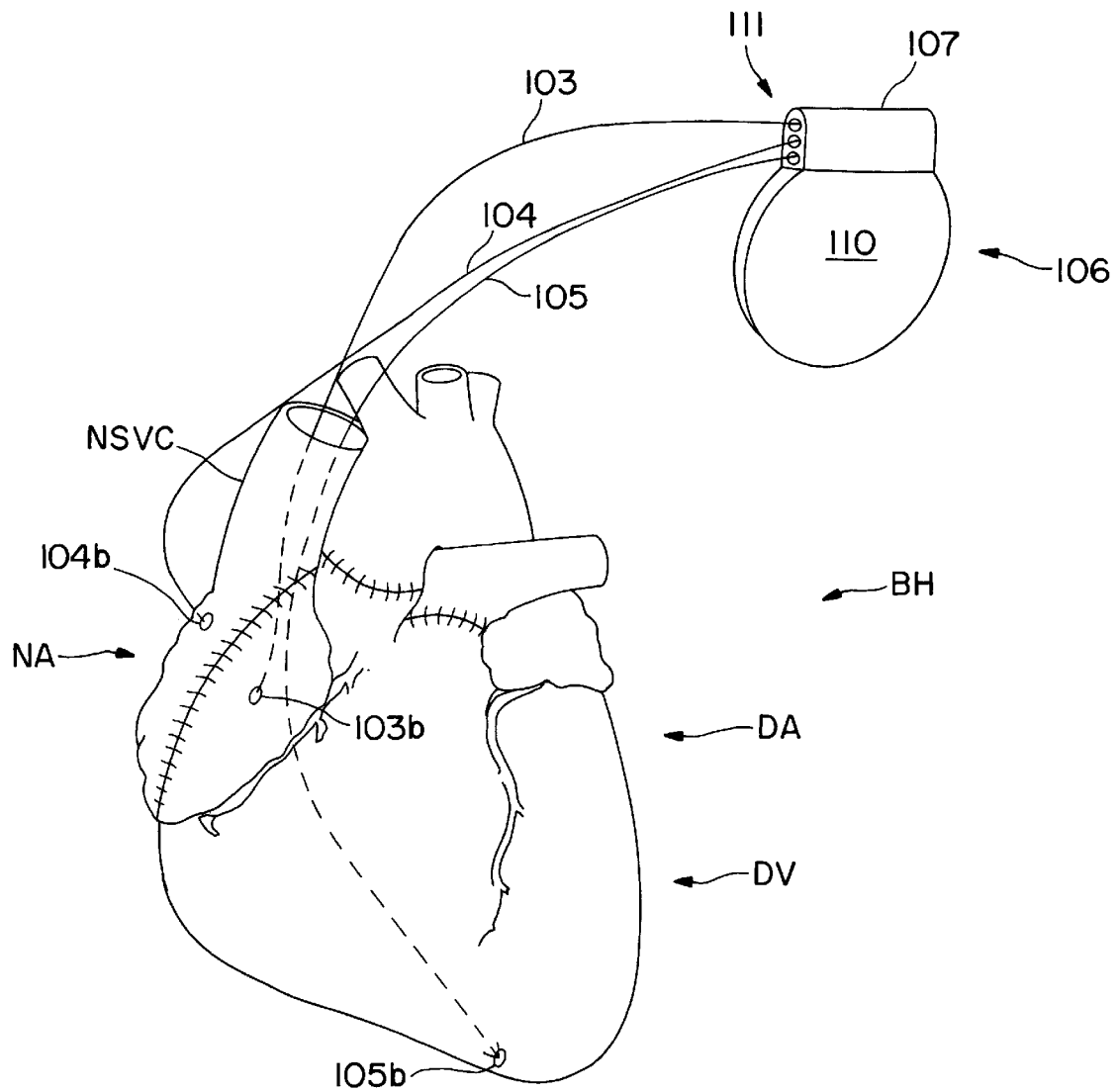

FIG. 1b, shows the use of the same device 106 for the alternate form of heart transplant mentioned above, orthotopic, in which the native atria (NA) are sewn onto the donor heart (DH) atop a portion of the donor atria (DA).The IPG circuitry, including sensors for rate response, programmability features and data storage elements are included within the shell or can 110. Reference may be had to the above cited pacemaker art for an indication of the state of the art with respect to such IPG features which are not of concern for the description of this invention although a generalized description is provided with reference to FIGS. 2 and 5 below. In FIG. 1b also the three bore connector block 107 is provided to connect leads 103–105 to their specialized circuits in the IPG can 110. Lead 105b is the ventricular lead and connects, preferably to the third of the three bores 111, nearest the pacemaker can. In one embodiment either unipolar atrial lead may be connected to the top and middle bores, but this requires either an additional pacing amplifier or switches, so the preferred configuration will have the donor atrial lead in a fixed location and the native atrial lead in the remaining of the three bores when the device is in operational condition. The leads 103 and 104 connect to the heart at locations 103b and 104b, respectively, which may vary as desired by the surgeon. In other words the surgeon may chose to place epicardial leads or endocardial leads, and may do so for any of the three leads connecting the IPG to the heart, but it is of course expected that one of the atrial leads will be fixed to the NA, one to the DA and the ventricular lead to the DV, so as to enable pacing and sensing as desired.

Figure 2:
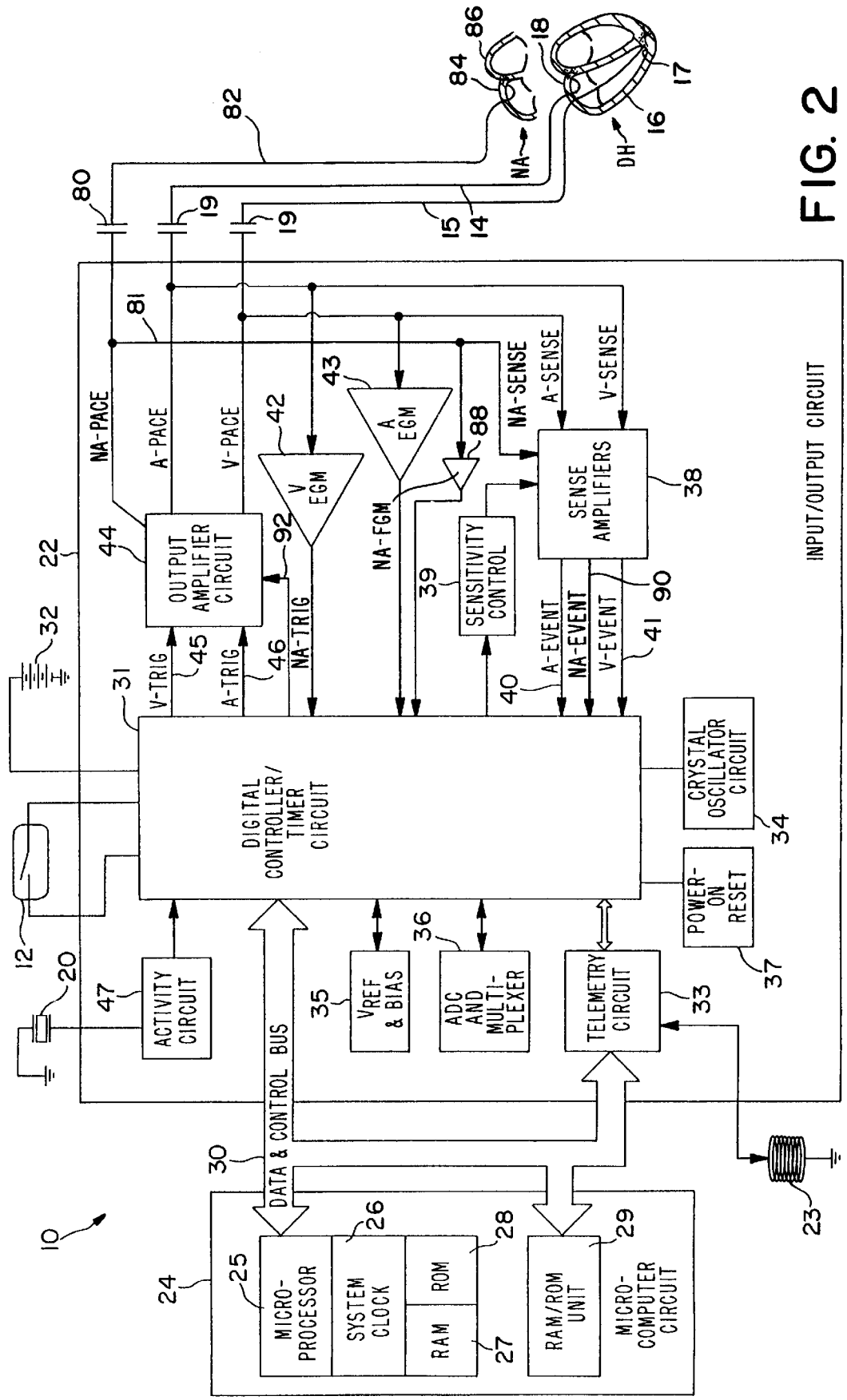
FIG. 2 is a block diagram of an implantable pulse generator in accordance with one embodiment of the present invention.

Referring to FIG. 2, there is shown a block diagram of an implantable pacemaker 10 with which the present invention may be advantageously practiced. Although the present invention will be described herein in the context of pacemaker 10, shown here connected to a native atrial portion (NA) and a donor heart (DH), it is to be understood that the following description is provided merely to illustrate the present invention in its various aspects. It is believed that the present invention may be advantageously practiced in conjunction with pacemakers used for native hearts, with various types of implantable devices other than pacemakers or what may be used together with pacemakers, such as defibrillators, nerve stimulators, and the like and associated implantable therapy delivery devices may additionally be associated therewith such as drug pumps and the like, and that those of ordinary skill in the art having the benefit of the present disclosure would be readily able to adapt the disclosed embodiments for use with such other devices. Moreover, although the present invention will be described herein in conjunction with a pacemaker 10 having a microprocessor-based architecture, it will be understood that pacemaker 10 (or other implanted device) may be implemented in any logic based, custom integrated circuit architecture, or custom analog component architecture, if desired. The pacemaker shown in FIG. 2 is substantially similar to that disclosed in U.S. Pat. No. 5,243,979 to Stein et al., entitled "Method and Apparatus for Implementing Activity Sensing in a Pulse Generator," the Stein '979 patent here being incorporated by reference herein in its' entirety. Another pacemaker with which the present invention may be advantageously practiced is disclosed in U.S. Pat. No. 5,052,388 to Sivula et al., entitled "Method and apparatus for Implementing Activity Sensing in a Pulse Generator." The Sivula et al. '388 patent is also hereby incorporated by reference herein in its' entirety. In FIG. 2, the preferred embodiment pacemaker 10 has an activity sensor 20, which may be, for example, a piezoelectric element bonded to the inside of the pacemaker's shield, although other sensors (like single or multi axis accelerometers) could be used. Such a pacemaker/activity sensor configuration is the subject of U.S. Pat. No. 4,485,813 to Anderson et al. Sensor 20 provides a sensor output which varies as a function of a measured parameter that relates to the metabolic requirements of a patient. Pacemaker 10 of FIG. 2 is programmable by means of an external programming unit 11 (not shown in FIG. 2, See FIG. 3 for example of programmer). One such 'programmer' suitable for the purposes of the present invention is the Medtronic Model 9760 programmer available from Medtronic, Inc., and is described with reference to U.S. Pat. Nos. 5,345,362 (Winkler), 5.549,654 (Powell) and Des 358,583 (Winkler). Other programmers may, of course, be used in applying the teachings of this invention. The 9760 programmer is a microprocessor based device which, for downlink telemetry, transmits a series of encoded signals to an implanted device by means of a programming head which transmits radio frequency (RF) encoded signals according to the telemetry system laid out, for example, in U.S. Pat. No. 5,127,404 to Wyborny et al. entitled "Telemetry Format for Implanted Medical Device"; which is assigned to the assignee of the present invention and which is incorporated herein by reference in its' entirety. For uplink telemetry, the implanted device transmits data using a pulse-position modulation scheme. Uplink telemetry data is transmitted byte-by-byte, with each byte being transmitted as a "frame" containing several RF bursts. The timing of the bursts within a frame indicates the type of data being transmitted, as well as the data itself. Although specific telemetry systems have been identified herein as being suitable for the purposes of practicing the present invention, it is to be understood, that the present invention is not specific to any one programming methodology. The Wyborny et al. '404 patent is identified herein for the purposes of illustration only, and it is believed to be within ordinary skill to adapt any programming protocol to provide uplink and downlink information effectively conveyed between pacemaker 10 and external programmer 11. As well, systems such as that shown in Body Bus Medical Device Communication System(U.S. Pat. No. 4,987,897 to Funke) could be used to avoid RF or E-field telemetry systems if desired. Similarly, it is believed that one of skill in the art would be able to choose from any of a number of available pacemaker programmers and programming techniques to accomplish the tasks necessary for practicing the present invention. As noted above, however, the Medtronic Model 9760 programmer is presently preferred.

In the illustrative embodiment of the present invention, parameters such as the lower rate of pacemaker 10 may be programmable, for example from 40 to 120 pulses per minute (PPM) in increments of 10 PPM, and the upper rate may be programmable, for example, between 100 and 175 PPM in 25 PPM increments. Those of ordinary skill in the art will appreciate that other information which may need to be communicated to implantable device in modern pacemakers may include at least: pacing mode, multiple rate response settings, electrode polarity, maximum and minimum pacing rates, output energy (output pulse width and/or output amplitude), sense amplifier sensitivity, refractory periods, calibration information, rate response attack (acceleration) and decay (deceleration), onset detection criteria, and perhaps many other parameter settings. The number of programmable parameters increases further for implantable devices, such as nerve and cardiac stimulators, cardiac assist devices combined with pacemakers, drug pumps combined with any of these, pacemaker/cardioverter/ defibrillators (PCDs), and so forth, which are operable in multiple therapy modes. Pacemaker 10 is schematically shown in FIG. 2 to be electrically coupled via pacing lead 14 and 15 to a donor heart 16. Leads 14 and 15 include one or more intracardiac electrodes, designated as 17 and 18 in FIG. 2, located near their distal ends of leads 14 and 15, respectively, and positioned within the right ventricular (RV) and right atrial (RA) chambers, respectively, of donor heart 16 (also labeled DH). Leads 14 and 15 can be of either the unipolar or bipolar type as is well known in the art; alternatively, a single, multiple electrode lead may be used. Another lead with a single electrode is preferably affixed to the native atria at 84 to provide sense and pace signals through the lead 82. This configuration of leads and electrodes is particularly suited to the transplant heart situation having native atria. For the orthotopic transplant, the ability to pace the native atria may not be useful but might be, and it would potentially assist in improving hemodynamic performance in the heterotopic transplant. Some other lead and electrode configurations besides the one shown in this FIG.

2 will be discussed below. It should be noted that since this device and system is designed for implantation into the patient during an open chest transplant operation, epicardial leads are readily substitutable for trans-venous leads to deliver pacing pulses or receive heart chamber depolarization information.

Tip electrodes 17 and 18 are coupled via suitable lead conductors through input capacitors 19 to input/output terminals of an input/output circuit 22. In the presently disclosed embodiment, activity sensor 20 is bonded to the inside of the pacemaker's outer protective shield, or may be located on a circuit board in the device as desired. As shown in FIG. 2, the output from activity sensor 20 is also coupled to input/output circuit 22. Input/output circuit 22 contains the analog circuits for interface to the heart 16, activity sensor 20, an antenna 23, as well as circuits for the application of stimulating pulses to heart 16 to control its rate as a function thereof under control of software-implemented algorithms in a microcomputer circuit 24 in a manner consistent with that in use in the art. This circuit is illustrative only and does not detail all the possible combinations of switches and leads and electrodes which may be employed. Illustrated here, leads 14, 15 and 82 appear to be single conductors, but they may be bipolar or even multipolar leads if the application of the inventive device requires them. Microcomputer circuit 24 comprises a microprocessor 25 having a system clock circuit 26, and RAM 27 and ROM 28. Microcomputer circuit 24 may preferably further comprise a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device or one augmented by standard components. Each of the electrical components represented in FIG. 2 is powered by an appropriate power source 32, in accordance with common practice in the art, which may preferably be a battery although numerous other possible power sources could be used, for example, kinetic power supplies such as power some watches from Seiko(their so-called Kinetic (TM) watches), or see for example U.S. Pat. No. 5,540,729, transferred power from an external coil to an internal coil for charging an internal rechargeable battery, large capacitor or other electrical storage device, and so on. For clarity, the coupling of power source(s) to the various components of pacemaker 10 has not been shown in the Figures.

Figure 3:
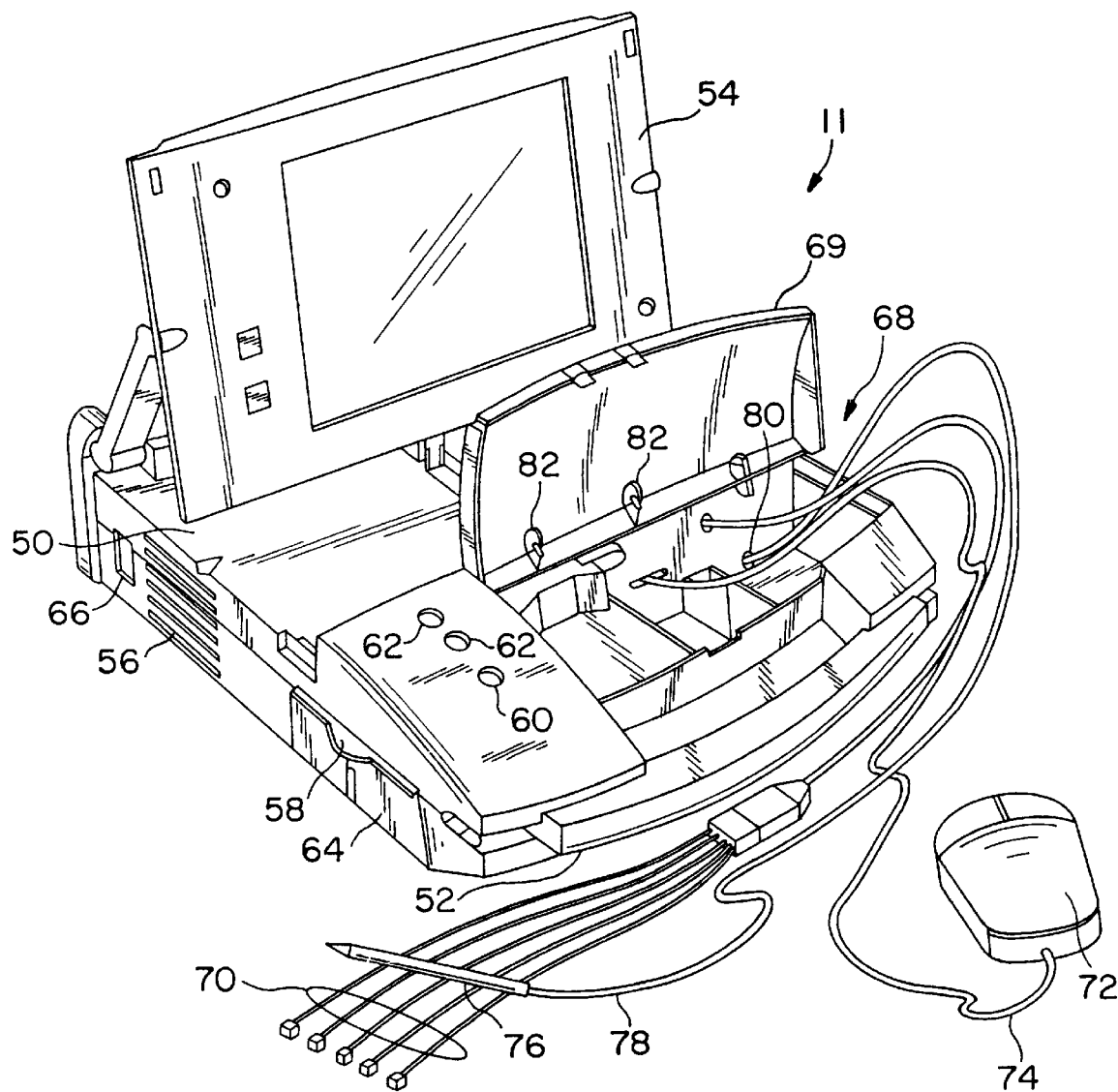
FIG. 3 is a perspective view of an external programming unit in accordance with the disclosed embodiment of the invention, used for communicating with the pulse generator of FIG. 1.

The microprocessor circuit may be controlled by programs stored in the memory circuits 27–29 and may be modified by the programmer of FIG. 3 as desired. Such programs are known in the art to control the values of timing variables and monitor capture, for example, and can be used for storing records of the device usage, patient condition vis-a-vis sensor readings, and so forth. In general it is well known to configure and reconfigure the timing circuitry on the fly by the direction or management of a controlling program which itself may be modified or updated by use of an external programmer as described in FIG. 3. It is the output of these programs that directs the timing of delivery of pacing pulses and the connection of or disconnection of the amplifiers to pace or sense activity in the heart tissue. All or any part of such directing and timing activity accomplished by a program may alternatively be directed by fixed analogue circuits, however currently digital programs are much preferred for their flexibility.

An antenna 23 is connected to input/output circuit 22 for purposes of uplink/downlink telemetry through an RF telemetry circuit 33. This is the antenna used for communication with the preferred programmer of FIG. 3. In the embodiment of FIG. 2, telemetry circuit 33 is coupled to digital controller/timer circuit 31, and includes circuitry generally in accordance with that disclosed in the Markowitz U.S. Pat. No. 4,374,382, such that event markers indicative of the occurrence of certain physiologic and pacer events may be transmitted to external programming unit 11. It is contemplated that telemetry circuit 33 may also be coupled directly to microcomputer circuit 24 via data and control bus 30. Alternative forms of communication may be employed such as the Funke body bus mentioned above or any other known communications strategy can be used, but presently the type described in the Markowitz '382 patent is preferred. A reed switch 12 is also coupled to input/output circuit 22. Although reed switch closure is no longer employed as the primary means of noninvasively communicating with an implanted device, reed switches may often still supplement the telemetry system.

For example, reed switch closure may be required before a telemetry link can be established, as a safeguard against spurious programming of the device. Reed switch closure may also cause the device to enter into a default mode of operation, sometimes referred to as "magnet mode," so that device operation remains consistent during programming or interrogation sessions, or for activating other special modes. A crystal oscillator circuit 34, typically a 32,768-Hz crystal-controlled oscillator, provides main timing clock signals to digital controller/timer circuit 31, if the microprocessor clock circuit (system clock 26) is not shared. A voltage reference (VREF) and Bias circuit 35 generates stable voltage reference and bias currents for the analog circuits of input/output circuit 22. An analog-to-digital converter (ADC) and multiplexor unit 36 digitizes analog signals and voltages to provide "real-time" telemetry intracardiac signals and battery end-of-life (EOL) replacement function. A power-on-reset (POR) circuit 37 functions as a means to reset circuitry and related functions to a default condition upon detection of a low battery condition, which will occur upon initial device power-up or can transiently occur in the presence of electromagnetic interference, for example. The operating commands for controlling the timing of pacemaker 10 are coupled by bus 30 to digital controller/timer circuit 31 wherein digital timers and counters are employed to establish the overall escape interval of the pacemaker, as well as various refractory, blanking, and other timing windows for controlling the operation of the peripheral components within input/output circuit 22. Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41and a native atrial event (NA-EVENT) signal on line 90. Sense amplifier circuit 38 is coupled to leads 14, 15, and 82 in order to receive the V-SENSE (ventricular sense) and A-SENSE (atrial sense) signals from donor heart 16 and to receive the N A-SENSE from the native heart (or native heart remnants)86. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected and a signal on line 90 for an NA EVENT. Sense amplifier circuit 38 includes one or more sense amplifiers corresponding, for example, to that disclosed in U.S. Pat. No. 4,379,459 issued to Stein, incorporated by reference herein in its' entirety.

Sensitivity control 39 is provided to adjust the gain of sense amplifier circuitry 38 in accordance with programmed sensitivity settings, as would be appreciated by those of ordinary skill in the pacing art. A V-EGM (ventricular electrocardiogram) amplifier 42 is coupled to lead 14 to receive the V-SENSE signal from donor heart 16. Similarly, an AEGM (atrial electrocardiogram) amplifier 43 is coupled to lead 15 to receive the A-SENSE signal from donor heart 16. Lastly, a NA-EGM (native AEGM) amplifier 88 is coupled to lead 82 to receive the native A-SENSE signal from native heart 86. The electrogram signals developed by V-EGM amplifier 42, NA-EGM amplifier 88, and A-EGM amplifier 43 are used on those occasions when the implanted device is being interrogated by external programmer 11, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference. Digital controller and timer circuit 31 is coupled to an output amplifier circuit 44 via three lines 45, 46, and 92, designated V-TRIG (ventricular trigger), A-TRIG (atrial trigger), and NATRIG (native atrial trigger), respectively. Circuit 31 asserts the V-TRIG signal on line 45 in order to initiate the delivery of a ventricular stimulating pulse to heart 16 via pace/sense lead 14. Likewise, circuit 31 asserts the A-TRIG signal on line 46 to initiate delivery of an atrial stimulating pulse to heart 16 via pace/sense lead 15. Similarly, circuit 31 asserts the NA-TRIG signal on line 92 to initiate delivery of a native atrial stimulating pulse to heart 86 by way of pace/sense lead 82. Output amplifier circuit 44 provides a ventricular pacing pulse (V-PACE) to the right ventricle of heart 16 in response to the VTRIG signal developed by digital controller/timer circuit 31 each time the ventricular escape interval times out, or an externally transmitted pacing command has been received, or in response to other stored commands as is well known in the pacing art. Also output amplifier circuit 44 provides an atrial pacing pulse (A-PACE) to the right atrium of heart 16 in response to the A-TRIG signal developed by digital controller/timer circuit 31. Similarly, output amp 44 provides a native atrial pacing pulse (NA-PACE) to the atrium of heart 86 responsive to the N A-TRIG signal from the digital controller/timer circuit 31. Output amplifier circuit 44 includes one or more output amplifiers which may correspond generally to that disclosed in U.S. Pat. No. 4,476,868 issued to Thompson also incorporated herein by reference in its' entirety. As would be appreciated by those of ordinary skill in the art, input/output circuitry will include decoupling circuitry for temporarily decoupling sense amplifier circuit 38, V-EGM amplifier 45, A-EGM amplifier 46, and N A-EGM amplifier circuit 88 from leads 14, 15, and 82 when stimulating pulses are being delivered by output amplifier circuit 44. For the sake of clarity, such decoupling circuitry is not depicted in FIG. 2.

An additional feature that is available with the use of three sense circuits is that of monitoring the donor atrium for capture. The IPG doesn't have to merely wait until the sinus rate from the native atrium requires another pace or alternatively wait for the next sensor indicated rate pace, but it can determine if the donor atrium has initiated it's own depolarization shortly after the delivery of the pacing pulse to it (i.e. after the atrial blanking period is expired) and if it detects such an event, it can reasonably assume that the donor atrium has not been captured. It can use such an occurrence to trigger a threshold search in the donor atrium using a variation of already known thresholding and capture detection techniques and algorithms, for example the ones described in the Markowitz et al. patent (U.S. 5,601,615), also incorporated herein by this reference.

While specific embodiments of sense amplifier circuitry, output amplifier circuitry, and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart as set forth just above. It is also believed that those of ordinary skill in the art could chose from among the various well-known implementations of such circuits in practicing the present invention.

Furthermore, data from any of the sense amps may be digitized, for example by circuit 36 and stored in memory so as to provide monitoring information to attending physicians when retrieved by telemetry as described above. Programs which use this data to monitor the health of the patient and cardiac performance generally are known for example, the Wahlstrand '974, Bennett'966, Steinhaus '028 Gebheardt '480 and Davies '707 patents cited above. They may reside fully within the pacemaker memory and run by the pacemaker microprocessor, or under control and in the memory of an external device such as a programmer (FIG. 3) or across some combination of devices.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. '388 U.S. patent. It is to be understood that the inclusion of an activity circuit in pacemaker 10 is not an essential feature of the present invention. The presence of an activity circuit is noted herein as but one example of the sophisticated operational capabilities of state-of-the-art implanted devices which make the devices' responses to physiological conditions complex and difficult to interpret. Also, the use of an activity circuit represents only one of a range of additional sensor circuits which could be included to provide additional information to the implanted device. Such additional sensors available currently include multi-axis accelerometers, oxygen sensors, pressure sensors, heart wall motion sensors, temperature sensors and the like. It is also to be noted that such sensor devices may be included on or in one of the leads so as to be advantageously placed in a particular area of the body suitable to that sensor.

In accordance with conventional practice, pacemaker 10 from FIG. 2 communicates via RF telemetry with an external programming unit 11, an example of which is illustrated in FIG. 3. Internally, programmer 11 includes a processing unit (not shown in the Figures) which in accordance with the presently disclosed embodiment of the invention is a personal computer type motherboard, e.g., a computer motherboard including a processor such as an Intel 80486 microprocessor and related circuitry such as digital memory. The details of design and operation of the computer system will not be set forth in detail in the present disclosure, as it is believed that such details are well-known to those of ordinary skill in the art. For the purposes of the present disclosure, it suffices to state that programmer 11 is capable of performing at least the types of operations of which the Medtronic Model 9760 programmer is capable. Referring to FIG. 3, programmer 11 comprises an outer housing 50, which is preferably made of thermal plastic or another suitably rugged yet relatively lightweight material. A carrying handle, designated generally as 52 in FIG. 3, is integrally formed into the front of housing 50. With handle 52, programmer 11 can be carried like a briefcase. An articulating display screen 54 is disposed on the upper surface of housing 50. Display screen 54 folds down into a closed position (not shown) when programmer 11 is not in use, thereby reducing the size of programmer 11 and protecting the display surface of display 54 during transportation and storage thereof. A floppy disk drive is disposed within housing 50 and is accessible via a disk insertion slot (not shown). A hard disk drive is also disposed within housing 50, and it is contemplated that a hard disk drive activity indicator, (e. g., an LED, not shown) could be provided to give a visible indication of hard disk activation. As would be appreciated by those of ordinary skill in the art, it is often desirable to provide a means for programmer 11 to adapt its mode of operation depending upon the type of implanted device to be programmed. Accordingly, it may be desirable to have an expansion cartridge containing EPROMs or the like for storing program information to control programmer 11 to operate in a particular manner corresponding to a given type of implantable device.

Either way the electrodes are used, if the application is to support pace a transplant heart, the sinus node of the native atria may be checked with one of the atrial electrodes for regularity(either by a doctor checking the electrograms or by timing and software processors in the device itself), and if successful used to overdrive pace the ventricles and to pace the transplant's atria in synchrony as well. Sensing can be done in the transplant's atria or they can be timed to have a very short delay from the sensed events in the native atria. The reader is referred to an article in PACE magazine, Vol. 17, Pg. 1974-9, Nov. 1994 by Cazeau et al. called FOUR CHAMBER CARDIAC PACING IN DILATED CARDIOMYOPATHY, which describes the use of four chamber pacing and TIMING OF RECIPIENT ATRIAL CONTRACTION AND ITS RELATION TO OPTIMAL DIASTOLIC FUNCTION AFTER HEART TRANSPLANTATION by Nagy et al, published in the European JCPE Vol. 6, No. 1, Pg. 301, Jun. 1, 1996. In general, and with any of the appropriate embodiments described above, for heart transplant pacing the preferred mode would be AATR pacing with a bi-atrial rate responsive pacemaker, the native atria operation to trigger the atrial pulse to the implanted chambers. When a native intrinsic sense signal occurs the recipient atria are preferably paced immediately thus allowing synchronizing of the atria and increasing cardiac output. Additionally, the addition of fallback to lower or sensor driven rate when high implant rate or native atrial fibrillation is detected should be included. Another way to view this is as a DDDR pacemaker with zero AVDelay(that is, the native atria provide the timing of the ventricle stimulus in the transplant, but upon detection of native atrial fibrillation, the sensor driven rate is used for the VV interval). A pacer with an epicardial lead to the LV used this mode in the Cazeau article above. Additional reference can be had to FIG. 5 where the chart has the NA (native atrial), DA (donor atrial) and DV (donor ventricular) electrograms lined up in time. The native atrial contraction at 402 initiates or triggers a pacing stimulus from the device, and causes a donor atrial contraction 404. An AV interval, if required to stimulate the DV (Donor Ventricle), can be timed from either T1 or T2 as shown. T1 and T2 may be fired off together if the native sinus rhythm is not good, to potentially improve cardiac hemodynamic performance.

Figure 4:
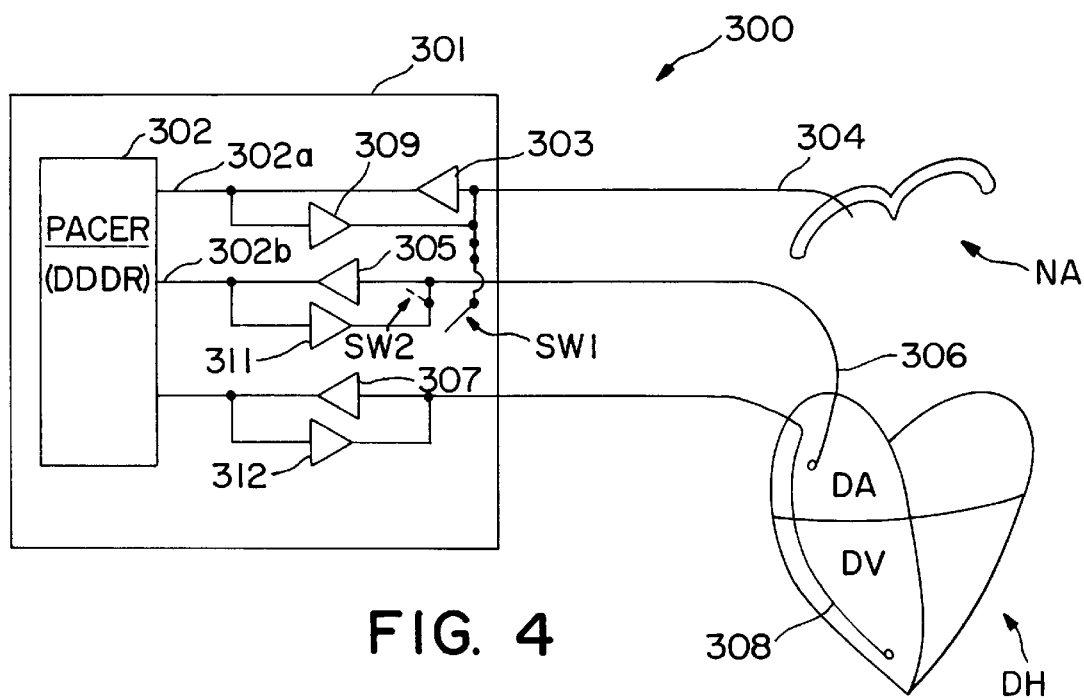
FIG. 4 is a simplified block diagram of a preferred form of the invention.

In FIG. 4, the inventive pacer device 301 and the native atria (NA) and donor heart (DH) form a native sinus rate driven pacing system 300, the depolarization by the native atrium NA to which lead 304 is attached providing input to sense amplifier 303. If the pacer determines the signal is sufficiently strong and regular and not widely off the mark relative to a rate responsive or sensor rate if the pacer 301 has one, then it will use the rate of received indications of native atrial depolarizations to time the pacing of the donor heart. In the simplest system, such as would be available using a commonly available modern pacemaker, there is no need for any lead to the atrium in the donor heart, because ventricular pacing may be sufficient to sustain life. However it is preferred to provide an additional lead for pacing the donor atrium. A most preferred form would also be able to sense in the donor atrium if only to perform atrial capture detection or far field intracardiac electrograms. Thus illustrated is lead 306, providing an electrical connection to sense amplifier 305 for reporting to the controlling electronics of the pacer 302 on electrical activity in the donor atrium. For pacing the donor atrium, a pacing pulse amplifier can provide sufficient electrical energy to capture the heart in a manner well known in the art. In the block diagram of FIG. 4 no indication of the operation of switches or blanking periods is shown since many such setups are available and known to the pacing art for modern DDD pacemakers. Pacing and sensing in the donor ventricle is done in a similar manner through lead 308, sense amplifier 307 and pacing amplifier circuit 312.

It should be noted that there are at least two ways to build a useful device. Both of these are illustrated in this figure wherein either a set of two switches sw1 and sw2 operate to bring the output of amp 311 to either conductive unipolar lead 304 or 306; or the addition of the third amplifier simplifies this and directs pacing pulses across line 304 while lead 306 gets it's pacing pulses from the output of amp 311. The addition of the additional or third amplifier allows for pacing the native atrium at a time suitable to provide additional hemodynamic benefit to for example, the heterotopic transplant by pumping blood into the remaining native ventricle at a time slightly before the donor atrium is paced, providing the maximum cardiac assistance from the donor ventricles. In any event, the addition of separate sense amps 303 and 305 provides for the ability to sense in both atria to provide capture detection and thresholding capabilities, vis-a-vis the donor atrium, or the native atrium for that matter, that are unavailable with a single atrial amplifier.

It should also be noted that using a circuit such as the one in FIG. 4, one could also use a bipolar two lead bore connector block for connecting the leads 304, 306 through a single atrial bore to the two lines 302*a* and 302*b*, if the lead is split as in the Limousin patents cited above. This would accommodate the functionality of doubled atrial amplifier circuitry as in FIG. 4, the usefulness of which is described above, with the expedient of a single lead to connector block connection. However it is believed that surgeons will prefer the three bore connector block, so this is mentioned as an alternative embodiment.

Figure 5:
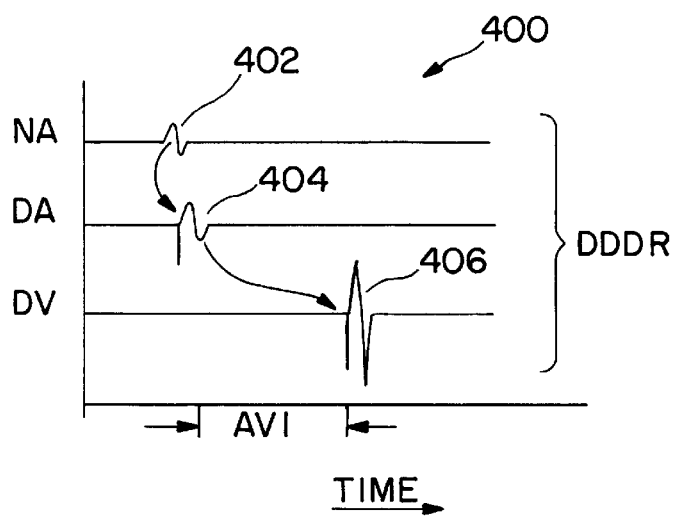
FIG. 5 is a chart of three time-coincident electrograms.

For convenient reference a timing diagram is provided in FIG. 5 in which a preferred timing sequence for tracking a sinus beat 402 with a captured donor atrial paced depolarization occurring at 404, yielding, after an AV interval, a paced ventricular response(Rwave) 406.

It should be recognized that during the transplant operation the surgeon has access to the entire epicardium and by positioning the pacing leads among paired chambers and connecting them epicardially, both the donor atria and/or donor ventricles may be paced by the same electrical pulse if both leads pace "unipolar", that is, tip to can. Thus, if the surgeon has the option of planting a leads' unipolar tip electrode at a point in or on the heart likely to trigger both atria (with the atrial lead) or both ventricles(with the ventricular lead) , additional hemodynamic benefit may be gained.

An additional benefit to be had from a pacemaker or implantable pulse generator designed in accord with the teachings of this invention may be had in that the need for monthly biopsies of the donor heart to determine the progress of tissue rejection can be attenuated or eliminated. Either the processing and time based analysis of intracardiac electrograms taken between the donor atrium and donor ventricular leads which is processed in accord with a program as described in Steinhaus et al,.'s U.S. Pat. No. 5,139,028 may be employed or direct evaluation of the strength or signal morphology of a particular characteristic of the waveform sensed by one of the three available input amplifiers as in Whalstrand et al's U.S. Pat. No. 5,402,794 to determine the rejection status of the donor heart. Implementation of such schemes as are described by these patents is not difficult with the use of the microprocessor and memory for storing a value or set of values representing the portion of the depolarization waves deemed useful in the particular analysis adopted, or in the Whalstrand method, either the amplitude or other waveform morphological characteristic could be stored for later output by telemetry or checked directly at monthly or semi-monthly follow ups, wherein the telemetric output contains the information sought. These two patents are incorporated by reference. It should be is noted that numerous other similar designs for analyzing cardiac depolarization waves or EKG's could also be used to provide a measure of the degree of rejection or overall health of the donor heart. It should also be noted that the instant invention uses one device not two, has less leads than would be required in either of these two cited systems and would be less costly to implement than either of them.

Thus a new system is disclosed that allows tracking of the native sinus rate, improves cardiac output and limits inappropriate pacing in the presence of arrhythmias in transplant patients, while allowing for transplant rejection monitoring. The inventive system is not to be considered limited in any way not set forth in the following claims.

What is claimed is:

1. An implantable medical pacemaker comprising an implantable pulse generator with sensing, pacing, and control circuitry housed therein and for providing electrical stimulus pacing pulses so as to drive a heart rate in a transplanted or donor heart having atrial and ventricular tissue, and wherein atrial tissue from a native heart is present in a patient, said pacemaker being adapted and disposed for electrical connection by three leads to three points of said hearts' tissue through three lead bores located in a connector block providing electrical connection to said sensing and pacing circuitry, a first lead for sensing a sinus rhythm in the native atrial tissue by connection thereto, a second lead for delivering atrial pacing pulses from said pacemaker to atrial tissue of said transplanted heart, and also by a third lead connectable to said native atrial tissue so as to provide a connection from said native atrial tissue to said sensing circuitry for sensing depolarizations of said native atrial tissue so as to enable timing circuitry in said control circuitry to determine when to provide pacing pulses to said donor atrial tissue and said donor ventricular tissue so as to provide both improved hemodynamics and chronotropic competence for the transplant patient in accord with a program for configuring said control circuitry.

2. A pacemaker as set forth in claim 1 wherein said sensing circuitry comprises a sensor for providing a signal to said pacemaker representative of cardiac demand of a patient, and program means for basing said stimulating pulses timing on said cardiac demand during times when said pacemaker cannot track said native atrial tissue sinus rate.

3. A pacemaker as set forth in claim 1 wherein said pacemaker has sensor for providing a signal to said pacemaker representative of cardiac demand of a patient, and program means for basing said stimulating pulses timing on said cardiac demand during times when said pacemaker cannot track said native atrial tissue sinus rate and when said sinus rate is inadequate for sensed cardiac demand.

4. A pacemaker as set forth in claim 1 and comprising:
   means for determining donor cardiac tissue rejection having signal generating means for communicating the status of said rejection, and
   means for transmitting information on said status to a receiver outside said the patient.

5. A pacemaker as set forth in claim 4 and wherein said means for determining rejection further comprises means for interpreting variations in timing and morphology of signals derived from said donor heart tissue and memory means for storing a value representative of said interpretation.

6. A pacemaker as set forth in claim 1 wherein said control circuitry further comprises capture detection program means for determining whether stimulation pulses delivered to donor atrial tissue has caused depolarizations thereof.

7. A pacemaker comprising an implantable pulse generator with sensing, pacing, and control circuitry housed therein and having two atrial sense amplifier circuits and one ventricular amplifier sense circuit, the output of each of which can be read independently by circuitry in said pacemaker and a connector block with three lead bores:
   a first lead connector bore adapted and disposed to provide electrical connection between a native atrial sense amplifier circuit in said pacemaker and a lead connected to a native atrium,
   a second lead connector bore adapted and disposed to provide electrical connection between a donor atrium and a donor atrium sense amplifier circuit in said pacemaker, and
   a third lead connector bore adapted and disposed to provide electrical connection between a donor ventricle and a donor ventricular pacing amplifier circuit.

8. A pacemaker as set forth in claim 7 and further comprising a ventricular sense circuit for sensing electrical activity of the donor ventricle through an electrical connection in said third lead connector bore.

9. A pacemaker as set forth in claims 7 or 8 and further comprising an atrial pace amplifier circuit connected to supply pacing pulses to said donor atrium through an electrical connection in said second lead connector bore.

10. A pacemaker comprising an implantable pulse generator with sensing, pacing, and control circuitry housed therein and having two atrial sense amplifier circuits, one for a donor atrium and one for a native atrium, and one ventricular amplifier sense circuit, and a connector block with two lead bores:
   a first lead connector bore adapted and disposed to provide electrical connection between a native atrial sense amplifier circuit in said pacemaker and one side of a split lead connected to a native atrium and also adapted and disposed to provide electrical connection between a donor atrium and a donor atrium sense amplifier circuit in said pacemaker through the other side of said split lead, and a second lead connector bore adapted and disposed to provide electrical connection between a donor ventricle and a donor ventricular pacing amplifier circuit.

11. A pacemaker as set forth in claims 10 or 7 further comprising a pacing amplifier connected to pace the donor atrium.

12. An implantable device as set forth in claim 11 wherein said atrial pacing amplifier is switchably connectable between said donor and a patient's native atrium.

* * * * *